United States Patent [19]
Behner et al.

[11] Patent Number: 5,559,139
[45] Date of Patent: *Sep. 24, 1996

[54] SPECIFIC 1,4-DIHYDROPYRIDINE-3,5-DICARBOXYLIC ACID ESTER, AND ITS PHARMACEUTICAL USE

[75] Inventors: Otto Behner; Hartmund Wollweber, both of Wuppertal; Bruno Rosen, Wuelfrath; Siegfried Zaiss; Siegfried Goldmann, both of Wuppertal, all of Germany

[73] Assignee: Bayer Aktiengesellschaft, Leverkusen, Germany

[*] Notice: The term of this patent shall not extend beyond the expiration date of Pat. No. 5,234,935.

[21] Appl. No.: 90,722

[22] Filed: Jul. 13, 1993

[30] Foreign Application Priority Data

Jul. 20, 1992 [DE] Germany .......................... 42 23 867.6

[51] Int. Cl.[6] ...................... C07D 211/86; A61K 31/455
[52] U.S. Cl. ............................................. 514/356; 546/321
[58] Field of Search ............................. 546/321; 514/356

[56] References Cited

U.S. PATENT DOCUMENTS

| | | | |
|---|---|---|---|
| 3,773,773 | 11/1973 | Bossert | 546/321 |
| 3,883,543 | 5/1975 | Bossert | 546/321 |
| 3,956,341 | 5/1976 | Loev | 546/321 |
| 4,780,538 | 10/1988 | Pitzenberger et al. | 546/249 |
| 4,975,440 | 12/1990 | Flockerzi et al. | 546/194 |
| 5,234,935 | 8/1993 | Behner et al. | 514/356 |
| 5,342,847 | 8/1995 | Behner et al. | 514/356 |
| 5,432,185 | 7/1995 | Behner et al. | 546/321 |

FOREIGN PATENT DOCUMENTS

| | | |
|---|---|---|
| 0234776 | 9/1987 | European Pat. Off. . |
| 0451654 | 10/1991 | European Pat. Off. . |
| 2210667 | 9/1973 | Germany . |

*Primary Examiner*—Jane Fan
*Attorney, Agent, or Firm*—Sprung Horn Kramer & Woods

[57] ABSTRACT

The invention relates to the new dimethyl 4-(4-chloro-3-trifluoromethylphenyl) -1-cyclopropyl-2,6-dimethyl-1,4-dihydropyridine-3,5-dicarboxylate, a process for its preparation and its use as a medicament in ischaemic diseases which are associated with disorders of the microcirculation. This action can occur both in the peripheral and in the cerebral vascular system.

3 Claims, No Drawings

SPECIFIC 1,4-DIHYDROPYRIDINE-3,5-DICARBOXYLIC ACID ESTER, AND ITS PHARMACEUTICAL USE

The invention relates to the new dimethyl 4-(4-chloro-3-trifluoromethylphenyl)-1-cyclopropyl-2,6-dimethyl-1,4-dihydropyridine-3,5-dicarboxylate, a process for its preparation and its use as a medicament in ischaemic diseases which are associated with disorders of the microcirculation. This action can occur both in the peripheral and in the cerebral vascular system.

It is already known that 1,4-dihydropyridinedicarboxylic acid esters have a calcium-antagonistic or calcium-agonistic action, and can thus be employed as vessel- and circulation-influencing agents (cf. U.S. Pat. No. 3,773,773)

EP 240,828 (U.S. Pat. No. 4,975,440) also describes hypotensive 1,4-dihydropyridines with haemorheological properties.

The present invention relates to the new dimethyl 4-(4-chloro-3-trifluoromethylphenyl)-1-cyclopropyl-2,6-dimethyl-1,4-dihydropyridine-3,5-dicarboxylate of the formula (I)

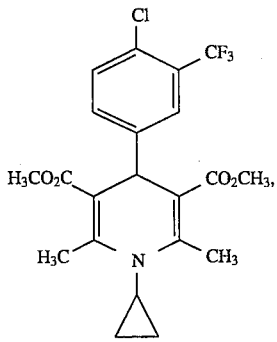

which surprisingly has a potent haemorheological action and improves the circulation, in particular the micro-circulation, and at the same time has a lack of effect on blood pressure. It is thus particularly suitable for use in the control of acute and chronic ischaemic disorders.

The compound of the formula (I) according to the invention can be prepared by customary methods, for example, by a process in which

[A] methyl (4-chloro-3-trifluoromethylbenzylidene)acetoacetate of the formula (II)

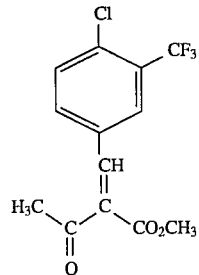

is reacted either directly with methyl 3-cyclopropylaminocrotonate, or with methyl acetoacetate and cyclopropylamine hydrochloride, in inert solvents or without solvents, if appropriate in the presence of a base/acid,
or

[B] 4-chloro-3-trifluoromethylbenzaldehyde of the formula (III)

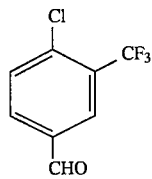

is reacted either with methyl acetoacetate and cyclopropylamine hydrochloride or cyclopropylamine anti pyridine hydrochloride respectively in pyridine,
or

[C] first, under a protective gas atmosphere, Lewis acids, preferably titanium tetrachloride, are treated with methyl 3-cyclopropylaminocrotonate in inert solvents using a base, preferably piperidine, and then 4-chloro-3-trifluoromethylbenzaldehyde of the formula (III) is added.

The process according to the invention can be illustrated by way of example by the following reaction scheme:

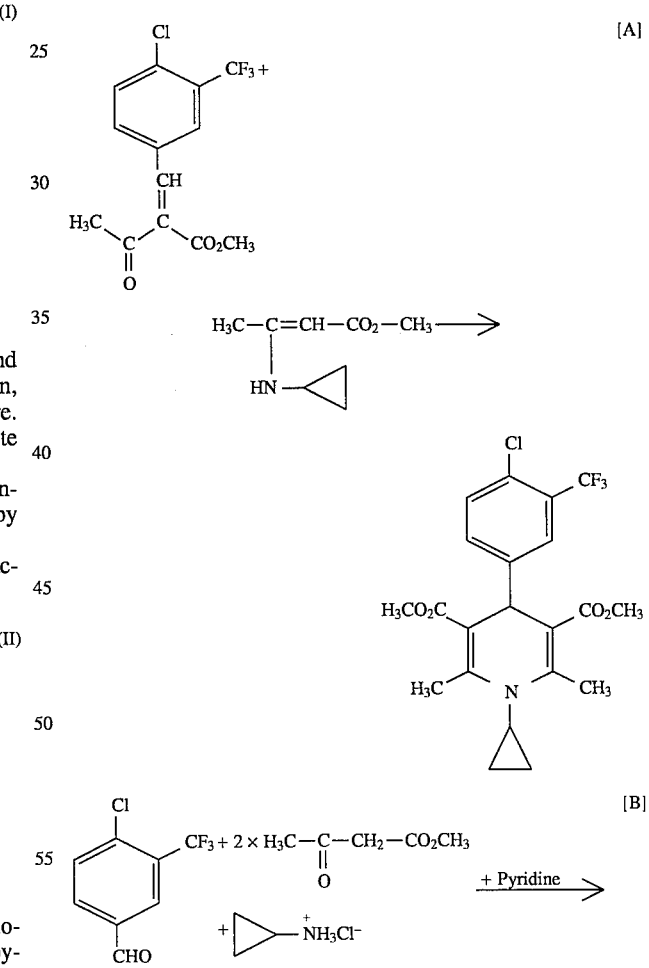

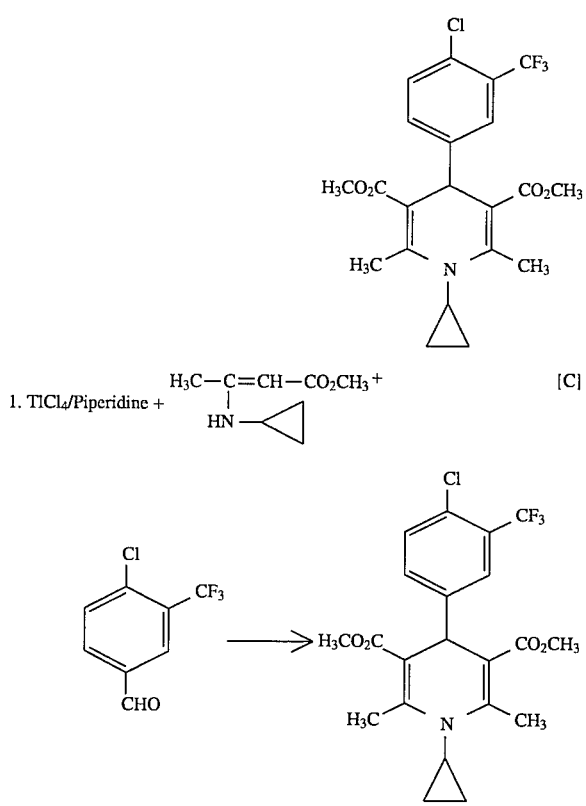

Possible solvents are water or organic solvents which do not change under the reaction conditions. These preferably include alcohols such as methanol, ethanol, propanol, isopropanol, butanol, ethers such as diethyl ether, dioxane, tetrahydrofuran, glycol monomethyl ether or glycol dimethyl ether, or amides such as dimethylformamide, dimethylacetamide or hexamethylphosphoramide, or glacial acetic acid, dimethyl sulphoxide, acetonitrile or pyridine. 1,2-Dimethoxyethane, butanol and pyridine are preferred.

Depending on the individual process steps, bases which can be employed are hydrides such as sodium hydride, alkali metal or alkaline earth metal hydroxides, such as, for example, sodium hydroxide or potassium hydroxide, alkoxides, such as potassium tert-butoxide, or pyridine. Sodium hydride and pyridine are preferred.

Acids employed are in general hydrochloric acid or sulphuric acid.

The reaction temperatures can be varied within a relatively wide range. In general, the reaction is carried out between +10° C. and +150° C., preferably between +20° C. and +120° C. in particular at the boiling point of the respective solvent.

The reaction can be carried out at normal pressure, but also at elevated or reduced pressure. In general, it is carried out at normal pressure.

When carrying out process variants A, B and C according to the invention, any desired ratio of the substances participating in the reaction can be used. In general, however, the reaction is carried out with molar amounts of the reactants. The substances according to the invention are preferably isolated and purified by distilling off the solvent in vacuo and recrystallising the residue, which may be obtained in crystalline form only after ice-cooling, from a suitable solvent. In some cases, it may be necessary to purify the compound according to the invention by chromatography.

The compounds of the formulae (II) and (III) are known.

The new compound according to the invention shows an unforeseeable, useful spectrum of pharmacological action. While it shows a lack of vasal and blood pressure effects in a dose range up to at least 10 mg/kg i.v. and 30 mg/kg p.o., it increases the circulation, in particular the microcirculation, by influencing the deformability of the erythrocytes and the inhibition of the activation and adhesion of the leucocytes.

The lack of effect on blood pressure is determined in the following models, which are typical for dihydropyridines: in SH rats after p.o. administration by measurement in the tail artery (Riva Rocci method) and in anaesthetised Wistar rats after i.v. administration. Measurement was carried out by means of a catheter in the carotid artery. This compound is designated as having a lack of effect on blood pressure, since it does not decrease the blood pressure in the two test models at the given dose. The difference between the therapeutic dose and a blood pressure action is at least a factor of 100.

The compound according to the invention can therefore be employed for the production of medicaments for the treatment of acute and chronic ischaemic disorders, such as intermittent claudication, myocardial infarct, cerebral infarct and also of reperfusion damage and shock.

The following in vitro and in vivo tests show the interesting actions of the specifically selected compound according to the invention.

I) Erythrocyte function

The deformability of erythrocytes plays a substantial role in the origin and the course of acute or chronic ischaemic disorders. They determine the viscosity of the blood and thus its distribution in the microcirculation. The tests used detect various determinants:

Test a) detects the antihaemolytic action of the substances ($ED_{50}$,mol/l). In this test, calcium-laden erythrocytes are pressed through small pores under high shearing stresses so that haemoglobin is released and measured as an expression of their haemolysis. The decrease in haemoglobin release is the quantity measured.

Test b) detects the viscosity of erythrocyte suspensions in glass capillaries (25 μm diameter) at low shearing stresses occurring in vessel areas behind a stenosis. Increasing the extracellular calcium increases the viscosity.

a) Antihaemolytic action in erythrocytes

Normal erythrocytes become haemolytic under high shearing stresses. The haemolysis of calcium-laden cells is particularly pronounced. This measure of mechanical stability is used for substance characterisation. The quantity measured is the concentration of free haemoglobin in the medium. The MEC is $5\times10^{-7}$ mol/l.

b) viscosity in glass capillaries

The biophysical interactions of erythrocytes relevant for the circulation can be investigated in glass capillaries (diameter 20–30 μm). The resulting viscosity depends on the condition of the cells. In the case of calcium loading the viscosity increases. The percentage improvement in the viscosity relative to a damaged, but untreated control at 0.7 Pa is given. The test dose is $10^{-8}$ g/ml.

TABLE I

| Example No. | Effect (%) |
|---|---|
| Compound (I) according to the invention | 72 |

II) Leucocyte function

The microcirculation can be directly observed in the hamster cheek pouch model. Quantities measured are leucocyte adhesion and also vessel diameter and erythrocyte sedimentation rate. Adhesion was quantified under ischaemic and non-ischaemic test conditions. Under non-ischaemic conditions, the adhesion is quantified in the area of small venules, under ischaemic conditions (10 min circulation stop) in small arterioles. The results of the control experiments are adjusted to 100%. The test dose selected is in each case 0.1 mg/kg i.v., the results are decreases in % of the control. Surprisingly, it appeared that under ischaemic conditions the substance also still acted at 0.1 mg/kg i.v. This is particularly favourable for the indications desired.

TABLE II

| Example No. | Non-ischaemic control = 100% | Ischaemic control = 100% |
|---|---|---|
| Compound (I) according to the invention | 50% | 49% |

III) Blood pressure

Clinical knowledge shows that antiischaemic actions of dihydropyridines are frequently masked by a vasodilatation. It was therefore the aim to find blood pressure-inactive (i.e. difference between haemorheological action and hypotensive action $\geq 10$) DHPs. The following Table shows the doses at which a blood pressure fall occurs on p.o. administration (SH rat) or i.v. administration (anaesthetised Wistar rat).

TABLE III

| Example No. | p.o. (mg/kg) | i.v. (mg/kg) |
|---|---|---|
| Compound (I) according to the invention | >90 | >10 |

The Table shows that, in comparison with model II, the difference between the therapeutic action and blood pressure action (i.v.) is at least 100.

The new active substance can be converted in a known manner into the customary formulations, such as tablets, coated tablets, pills, granules, aerosols, syrups, emulsions, suspensions and solutions, using inert, non-toxic, pharmaceutically suitable excipients or solvents. In this case, the therapeutically active compound should in each case be present in a concentration of about 0.5 to 90% by weight of the total mixture, i.e. in amounts which are sufficient to achieve the dosage range indicated.

The formulations are prepared, for example, by extending the active substances with solvents and/or excipients, if appropriate using emulsifiers and/or dispersants, where, for example, when using water as a diluent, organic solvents can optionally be used as auxiliary solvents.

Administration is carried out in a customary manner, preferably orally or parenterally, in particular perlingually or intravenously.

In general, it has proven advantageous on intravenous administration to administer amounts of about 0.001 to 1 mg/kg, preferably about 0.01 to 0.5 mg/kg of body weight, to achieve effective results, and on oral administration the dosage is about 0.01 to 20 mg/kg, preferably 0.1 to 10 mg/kg of body weight.

In spite of this, it may sometimes be necessary to deviate from the amounts mentioned, to be precise depending on the body weight or on the type of administration route, on individual behaviour towards the medicament, the manner of its formulation and the point or interval at which administration takes place. Thus, in some cases it may be sufficient to manage with less than the above-mentioned minimum amount, while in other cases the upper limit mentioned must be exceeded. In the case of the administration of relatively large amounts, it may be advisable to divide these into several individual doses over the course of the day.

PREPARATION EXAMPLES

Example 1

Dimethyl 4-(4-chloro-3-trifluoromethylphenyl)-1-cyclopropyl-2,6-dimethyl-1,4-dihydropyridine-3,5-dicarboxylate

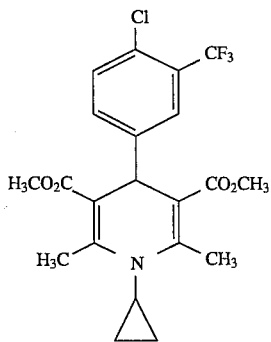

Process A

A solution of 23.3 g (0.15 mol) of methyl 3-cyclopropyl-amino-crotonate, 46.0 g (0.15 mol) of methyl (4-chloro-3-trifluoromethylbenzylidene)-acetoacetate and 17.7 g (0.15 mol) of pyridine hydrochloride in 100 ml of pyridine is stirred under reflux for 7.5 h. After evaporation in vacuo, the residue is partitioned between 120 ml of methylene chloride and 150 ml of water. After evaporation, the organic phase gives a resinons crude product, which is recrystallised from 100 ml of cyclohexane.

Melting point: 131°–135° C.

Yield: 35.0 g (52.6% of theory).

Process B

A solution of 4.17 g (0.02 mol) of 4-chloro-3-trifluoromethylbenzaldehyde, 4.65 g (0.04 mol) of methyl acetoacetate and 1.96 g (0.021 mol) of cyclopropylamine hydrochloride in 20 ml of pyridine is stirred under reflux for 4 h. After evaporation, the residue is partitioned between 40 ml of methylene chloride and 50 ml of water. An oily crude product is obtained from the organic phase by evaporation, and is crystallised using cyclohexane and n-pentane.

Melting point: 131°–134° C.

Yield: 3.33 g (37.5% of theory)

We claim:

1. Dimethyl 4-(4-chloro-3-trifluoromethylphenyl)-1-cyclopropyl-2,6-dimethyl-1,4-dihydropyridine-3,5-dicarboxylate.

2. A haemorheological composition comprising an amount effective therefor of a compound according to claim 1 and a pharmaceutically acceptable expedient or solvent.

3. In the administration to a patient of a microcirculation promoting compound, the improvement which comprises producing a haemorheological activity with substantially no vascular activity or effect on blood pressure by employing as such compound an effective amount of the compound according to claim 1.

* * * * *